United States Patent

Reinhardt et al.

Patent Number: 5,486,609
Date of Patent: Jan. 23, 1996

[54] PREPARATION OF CARBOCYLIC M-AMINOHYDROXYAROMATICS

[75] Inventors: Robert Reinhardt, Meckenheim; Helmut Reichelt, Neustadt; Roland Merger, Bad Schönborn, all of Germany

[73] Assignee: BASF Aktiengesellschaft, Ludwigshafen, Germany

[21] Appl. No.: 409,713

[22] Filed: Mar. 24, 1995

[30] Foreign Application Priority Data

Mar. 26, 1994 [JP] Japan .................. 44 10 660.2

[51] Int. Cl.$^6$ .................. C07D 265/30
[52] U.S. Cl. ............ 544/173; 546/240; 548/577; 564/394; 564/412; 564/413; 564/415; 564/442
[58] Field of Search ............ 544/173; 546/240; 548/577; 564/394, 415, 412, 413, 442

[56] References Cited

U.S. PATENT DOCUMENTS 2,062,349 12/1936 Calcott et al. .
3,873,573 3/1975 Farber et al. .
5,001,265 3/1991 Liu et al. .................. 564/418

OTHER PUBLICATIONS

CA 108: 23350b Benzophenonderivatives. Yonese et al., p. 78, 1988.
CA 119: 138868w Preparation . . . dihydroxybenzene. Kuwabara et al., p. 838, 1993.
Methoden der Organischen Chemie, Organische Stickstoff–Verbindungen IV, Band E16d, pp. 684–685, 1992.
J. Amer. Chem. Soc., (1952); pp. 3027–3029; Rearrangements in Animation by Alkali Amides . . . ether, Gilman et al.

*Primary Examiner*—Joseph K. McKane
*Attorney, Agent, or Firm*—Oblon, Spivak, McClelland, Maier & Neustadt

[57] ABSTRACT

A process for preparing carbocyclic m-aminohydroxyaromatics comprises reacting the corresponding o— or m-halohydroxyaromatics or metal salts thereof with primary or secondary amines in the presence of a base and in the presence or absence of a diluent.

6 Claims, No Drawings

PREPARATION OF CARBOCYLIC M-AMINOHYDROXYAROMATICS

The present invention relates to a novel process for preparing carbocyclic m-aminohydroxyaromatics by reacting the corresponding o— or m-halohydroxyaromatics with primary or secondary amines.

J. Amer. Chem. Soc., 74 (1952), 3027–29, discloses that the treatment of o-bromophenol with twice the molar amount of lithium diethylamide in boiling diethyl ether gives rise to m-diethyl-aminophenol. However, the process described there is completely unsuitable for an industrial synthesis, since m-diethylaminophenol is formed only in a yield of 15%.

It is an object of the present invention to provide a novel process for preparing carbocyclic m-aminohydroxyaromatics which gives the target products in a simple manner in high yield and purity.

We have found that this object is achieved by a process for preparing carbocyclic m-aminohydroxyaromatics, which comprises reacting carbocyclic o— or m-halohydroxyaromatics or metal salts thereof with primary or secondary amines in the presence of a base and in the presence or absence of a diluent.

Carbocyclic o— or m-halohydroxyaromatics include for example o— or m-halophenols and o— or m-halohydroxynaphthalenes.

Primary or secondary amines include for example primary or secondary saturated or unsaturated aliphatic, cycloaliphatic or aromatic amines.

The m-aminophenols or m-aminohydroxynaphthalenes preferably conform to the formula I

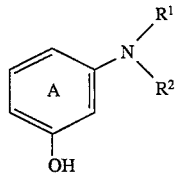

$R^1$ and $R^2$ are each independently of the other $C_1$–$C_{18}$ -alkyl, which may be substituted and may be interrupted by from 1 to 3 oxygen atoms in ether function or by from 1 to 3 $C_1$–$C_4$-alkylimino groups, $C_3$–$C_7$-cycloalkyl, $C_3$–$C_{18}$-alkenyl or substituted or unsubstituted phenyl, or $R^1$ and $R^2$ are together with the nitrogen atom joining them together a 5— or 6-membered saturated heterocyclic radical which may contain a further hetero atom, or else $R^1$ is hydrogen or $C_1$–$C_8$-alkanoyl, and the ring A may be substituted and may be benzofused.

The o— or m-halophenols or o— or m-halohydroxynaphthalenes preferably conform to the formula II

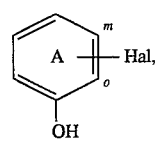

where Hal is halogen and the ring A is as defined above (in free form or as metal salt), and the o-compounds are of particular importance.

The primary or secondary aliphatic, cycloaliphatic or aromatic amines preferably conform to the formula III

where $R^1$ and $R^2$ are each as defined above.

Any alkyl or alkenyl appearing in the abovementioned formulae may be straight-chain or branched.

Alkenyl for the purposes of the present invention is to be understood as meaning essentially those radicals which have from 1 to 3 double bonds.

Any substituted alkyl appearing in the abovementioned formulae may have as substituents for example hydroxyl, amino or phenyl. The number of substituents in substituted alkyl is generally 1 or 2.

Any substituted phenyl appearing in the abovementioned formulae and any substituted ring A may have as substituents for example $C_1$–$C_4$-alkyl, hydroxyl, halogen or $C_1$–$C_4$-alkoxy. The number of substituents in substituted phenyl or a substituted ring A is generally from 1 to 3.

$R^1$ and $R^2$ combined with the nitrogen atom joining them together into a 5— or 6-membered saturated heterocyclic ring with or without a further hetero atom can be for example pyrrolidinyl, piperidinyl, morpholinyl, piperazinyl or N-($C_1$–$C_4$ -alkyl)piperazinyl.

$R^1$ and $R^2$ are each for example methyl, ethyl, propyl, isopropyl, butyl, isobutyl, sec-butyl, pentyl, isopentyl, neopentyl, tert-pentyl, hexyl, 2-methylpentyl, heptyl, octyl, 2-ethylhexyl, isooctyl, nonyl, isononyl, decyl, isodecyl, undecyl, dodecyl, tridecyl, 3,5,5,7-tetramethylnonyl, isotridecyl (the above designations isooctyl, isononyl, isodecyl and isotridecyl are trivial derived from the oxo process alcohols—cf. Ullmann's Encyclopedia of Industrial Chemistry, 5th Edition, Vol. A1, pages 290 to 293, and Vol. A 10, pages 284 and 285), tetradecyl, pentadecyl, hexadecyl, heptadecyl, octadecyl, 2-methoxyethyl, 2-ethoxyethyl, 2-propoxyethyl, 2-isopropoxyethyl, 2-butoxyethyl, 2— or 3-methoxypropyl, 2— or 3-ethoxypropyl, 2— or 3-propoxypropyl, 2— or 3-butoxypropyl, 2— or 4-methoxybutyl, 2— or 4-ethoxybutyl, 2— or 4-propoxybutyl, 2— or 4-butoxybutyl, 2-hydroxyethyl, 2— or 3-hydroxypropyl, 2— or 4-hydroxybutyl, 5-hydroxypentyl, 6-hydroxyhexyl, 5-hydroxy-3-oxapentyl, benzyl, 1-phenylethyl, 2-phenylethyl, 2-aminoethyl, 2— or 3-aminopropyl, 2— or 4-aminobutyl, cyclopropyl, cyclobutyl, cyclopentyl, cyclohexyl, methylcyclohexyl, cycloheptyl, allyl, propyl-en-1-yl, methallyl, ethallyl, pentenyl, pentadienyl, hexadienyl, 3,7-dimethylocta-6,1-dien-1-yl, undec-10-en-1-yl, 6, 10-dimethylundeca-5, 9-dien-2-yl, 3, 7,11-trimethyldodeca-1, 6, 10-trien-1-yl, 3,7,11-trimethyldodeca-2, 6, 10-trien-1-yl, octadec-9-en-1-yl, octadeca-9, 12-dien-1-yl, octadeca- 9, 12,15-trien-1-yl, 6, 10,14-trimethylpentadeca-5,9,1,3-trien-2-yl, phenyl, 2-, 3- or 4-methylphenyl, 2-, 3- or 4-ethylphenyl, 2,4-dimethylphenyl, 2-, 3- or 4-methoxyphenyl, 2-, 3- or 4-ethoxyphenyl, 2,4-dimethoxyphenyl, 2-, 3- or 4-chlorophenyl, 2,4-dichlorophenyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 4,8-dioxadecyl, 3,6,8-trioxadecyl, 3,6,9-trioxaundecyl, 2-dimethylaminoethyl, 2-diethylaminoethyl, 2- or 3-dimethylaminopropyl, 2— or 3-diethylaminopropyl, 2— or 4-dimethylaminobutyl, 2— or 4-diethylaminobutyl, 3,6-dimethyl-3,6-diazaheptyl, 3,6,9-trimethyl-3,6,9-triazadecyl, 2-(1-methoxyethoxy)ethyl, 2-(1-ethoxyethoxy)ethyl, 2-(1-isobutoxyethoxy)ethyl, 2— or 3-(1-methoxyethoxy)propyl, 2or 3-(1-ethoxyethoxy)propyl or 2— or 3-(1-isobutoxyethoxy)propyl.

$R^1$ may also be for example formyl, acetyl, propionyl, butyryl, isobutyryl, pentanoyl, hexanoyl, heptanoyl, octanoyl or 2-ethylhexanoyl.

Carbocyclic o— or m-halohydroxyaromatics include for example the corresponding fluorine, chlorine or bromine compounds. The use of the chlorine or bromine compounds is preferred, and that of the chlorine compounds is particularly preferred.

In terms of the formula II, this means that preference is given to using those compounds of the formula II where Hal is chlorine or bromine, in particular chlorine.

As mentioned above, the carbocyclic o— or m-halohydroxyaromatics can be used in the process of the invention either in free form or in the form of their metal salts.

Suitable metal salts include for example the alkali or alkaline earth metal salts, such as lithium, sodium, potassium, magnesium or calcium salts.

When the carbocyclic o— or m-halohydroxyaromatics are used in the form of their metal salts, the use of the alkali metal salts, in particular the sodium or potassium salts, is preferred.

Suitable bases which can be used in the process of the invention include for example alkali or alkaline earth metal amides, alkali or alkaline earth metal alkoxides, alkali or alkaline earth metal hydrides or alkali or alkaline earth organometallic compounds. The use of alkali or alkaline earth hydroxides or alkali or alkaline earth oxides is also possible.

Suitable alkali or alkaline earth metal salts include for example the corresponding lithium, sodium, potassium, magnesium or calcium salts. The use of the alkali metal salts, in particular of the sodium or potassium salts, is preferred.

Suitable alkali or alkaline earth organometallic compounds include in particular the organolithium compounds, eg. methyl-, ethyl-, propyl-, butyl- or phenyl-lithium.

Suitable amides include for example the unsubstituted alkali or alkaline earth metal halides or those alkali or alkaline earth metal amides which are derived from amines of the formula $NHR^1R^2$ where $R^1$ and $R^2$ are each as defined above.

Suitable alkoxides are the alkali or alkaline earth metal alkoxides derived from $C_1$–$C_4$-alkanols, such as methanol, ethanol, propanol, isopropanol, butanol, isobutanol, sec-butanol or tertbutanol.

Suitable diluents for use in the process of the invention include for example the primary or secondary amine reactants, in excess. However, suitable diluents also include inert diluents, for example ethers, such as diethyl ether, methyl-tert-butyl ether, 1,2-dimethoxyethane, 1,2-diethoxyethane, tetrahydrofuran or dioxane, carboxamides, such as N,N-dimethylformamide or N,N-dimethylacetamide, or aliphatic or aromatic hydrocarbons, such as hexane, heptane, octane, isooctane, petroleum ether, naphtha, toluene, xylene, dodecylbenzene, diisopropylnaphthalene or a mixture of higher aromatics commercially available as Shellsol® AB (Shell).

The preferred base for use in the process of the invention is an alkali metal amide, preferably sodium or potassium amide, particularly preferably sodium amide.

The preferred diluent for use in the process of the invention is an excess of the primary or secondary amine reactant.

A preferred embodiment comprises reacting amines of the formula III where $R^1$ and $R^2$ are each independently of the other $C_1$–$C_{15}$-alkyl, which may be substituted and may be interrupted by from 1 to 3 oxygen atoms in ether function, cyclohexyl or substituted or unsubstituted phenyl, or $R^1$ and $R^2$ together with the nitrogen atom joining them together are a 5— or 6-membered saturated heterocyclic radical with or without a further hetero atom, or else $R^1$ is hydrogen.

A preferred embodiment further comprises reacting o-halophenols of the formula IIa

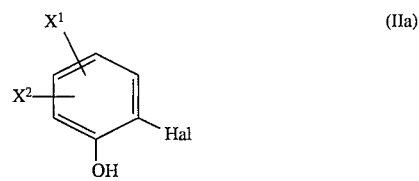

where Hal is chlorine or bromine, in particular chlorine, and $X^1$ and $X^2$ are each independently of the other hydrogen or $C_1$–$C_4$-alkyl, in particular hydrogen.

Particular preference is given to using in the process of the invention amines of the formula III where $R^1$ and $R^2$ are each independently of the other $C_1$–$C_6$-alkyl, cyclohexyl or phenyl, or $R^1$ and $R^2$ together with the nitrogen atom joining them together are a 5— or 6-membered saturated heterocyclic radical with or without a further hetero atom, or else $R^1$ is hydrogen.

Attention has to be drawn in particular to the use of the amines of the formula III where $R^1$ and $R^2$ are each independently of the other $C_1$–$C_6$-alkyl, in particular $C_1$–$C_4$-alkyl, or $R^1$ and $R^2$ together with the nitrogen atom joining them together are pyrrolidinyl, piperidinyl or morpholinyl, or else $R^1$ is hydrogen.

Based on 1 mol of carbocyclic o— or m-halohydroxyaromatic (in free form), the amount of base used in the novel process can be from 2 to 20 mol, preferably from 2 to 10 mol, in particular from 2.5 to 5 mol.

Based on 1 mol of carbocyclic o-halohydroxyaromatic (as metal salt), the amount of base used in the novel process can be from 1 to 20 mol, preferably from 1 to 10 mol, in particular from 1.5 to 5 mol.

The primary or secondary amines and the carbocyclic o— or m-halohydroxyaromatics should be used in the novel process at least in a molar ratio of 1:1, preferably at least 5:1, in particular at least 15:1.

Since, as mentioned above, the primary or secondary amines can also act as diluents, there is in principle no fixed upper limit to their amount, but for technical reasons the molar ratio of amine:o— or m-halohydroxyaromatic should generally not exceed 100:1.

As mentioned above, however, it is also possible to use inert diluents. Based on the weight of the carbocyclic o— or m-halohydroxyaromatic, the amount of inert diluent used is generally from 0 to 2000% by weight.

The process of the invention can be carried out at a temperature from $-50°$ to $+300°$ C., preferably from $0°$ to $+300°$ C., the particularly preferred upper limit of the temperature being dictated by the boiling point of whichever is the lowest boiling component in the reaction mixture.

Generally, the process of the invention is carried out at atmospheric pressure, but can also be carried out under a slight superatmospheric pressure (up to about 20 bar).

The novel process can be carried out continuously as well as batchwise.

Advantageously, with or without a protective gas, eg. nitrogen, atmosphere, the reactants, the base and any inert diluent are introduced into a suitable apparatus, eg. a stirred apparatus, in any desired order and treated at the abovementioned temperature until the o— or m-halohydroxyaromatic has been converted to the desired degree.

This is followed by cooling down to room temperature, adding water or methanol and workup of the reaction mixture in a conventional manner as also described in detail in the Examples, for example by distillation, crystallization, extraction or chromatographic methods.

The process of the invention is technically simple to carry out and gives the target product in good yield and isomeric purity. Compared with existing industrial methods for producing m-aminophenols, it is notable for its low number of stages (being single-stage).

The carbocyclic m-aminohydroxyaromatics produced by means of the process according to the invention are useful intermediates, for example for the synthesis of fluorans which are useful as color formers (see for example U.S. Pat. No. -A-3,873,573).

The Examples which follow illustrate the invention.

Example 1

150 ml of dry diethylamine under nitrogen were admixed with 6.2 g (150 mmol) of 95% by weight pure crystalline sodium amide by stirring at 20° C. for 5 min. Then 6.4 g (50 mmol) of 2-chlorophenol were added and the reaction mixture was refluxed for 3 h with stirring. After cooling down to 20° C., excess sodium amide was destroyed by the careful addition of 50 ml of water, and diethylamine was distilled off at an internal temperature of up to 100° C. The distillation residue was admixed with water, adjusted with concentrated hydrochloric acid to pH 7.0 and extracted with dichloromethane. Distillative removal of the solvent and drying of the combined extracts with sodium sulfate resulted in 7.7 g of a red oil which, according to GC, contained 1.9 g (30% of theory) of 2-chlorophenol and 5.4 g (65% of theory) of 3-diethylaminophenol. Based on the conversion of 2-chlorophenol, the yield of 3-diethylaminophenol is 93%.

Example 2

200 ml of dry diethylamine under nitrogen were admixed with 6.2 g (150 mmol) of 95% by weight pure crystalline sodium amide by stirring at 20° C. for 5 min. Then 6.4 g (50 mmol) of 3-chlorophenol were added and the reaction mixture was refluxed for 3 h with stirring. After cooling down to 20° C., excess sodium amide was destroyed by the careful addition of 5 ml of water, and diethylamine was distilled off at an internal temperature of up to 100° C. The distillation residue was adjusted with concentrated hydrochloric acid to pH 7.5 and, after addition of 5 ml of water and 150 g of dichloromethane, clarified by filtration. The organic phase was separated off and distilled, initially under atmospheric pressure, then under reduced pressure, to remove dichloromethane and further volatiles. This resulted in 14.0 g of a dark oil which, according to GC, contained 1.6 g (25% of theory) of 3-chlorophenol and 5.9 g (72% of theory) of 3-diethylaminophenol. Based on the conversion of 3-chlorophenol, the yield of 3-diethylaminophenol is 96%.

Example 3

150 ml of dry di-n-butylamine under nitrogen were admixed with 6.2 g (150 mmol) of 95% by weight pure crystalline sodium amide by stirring at 20° C. for 5 min. Then 6.4 g (50 mmol) of 2-chlorophenol were added, and the reaction mixture was stirred at 80° C. for 10 h and at 100° C. for 4 h. After cooling down to 20° C., excess sodium amide was destroyed by the careful addition of water, and the batch was extracted with diethyl ether. The combined extracts were distilled to remove diethyl ether and, under reduced pressure, di-n-butylamine to a substantial degree. This resulted in 10.9 g of an oil containing 3.1g of di-n-butylamine and 7.8 g (70% of theory) of 3-(di-n-butylamino)phenol (NMR).

Example 4

150 ml of dry morpholine under nitrogen were admixed with 6.2 g (150 mmol.) of 95% by weight pure crystalline sodium amide by stirring at 20° C. for 5 min. Then 6.4 g (50 mmol) of 2-chlorophenol were added, and the reaction mixture was heated to 80° C. for 2 h. After cooling down to 20° C., excess sodium amide was destroyed by the careful addition of 100 ml of water, and morpholine was distilled off under reduced pressure. The solution of the solid residue in water was adjusted with concentrated hydrochloric acid to pH 7.0 and extracted with dichloromethane. Distillative removal of the solvent after drying of the combined extracts with sodium sulfate resulted in 7.2 g of pale brown crystals having a melting point of from 120° to 123° C., which, according to GC, contained 6.1 g (68% of theory) of 3-morpholinophenol and 0.6 g of morpholine.

Example 5

125 ml of dry n-butylamine under nitrogen were admixed with 3.1 g (75 mmol) of 95% by weight pure crystalline sodium amide by stirring at 20° C. for 5 min. Then 3.6 g (25 mmol) of 2-chloro-4-methylphenol were added, and the reaction mixture was refluxed for 2 h with stirring. After cooling down to 20° C., excess sodium amide was destroyed with 10 ml of methanol, and n-butylamine was distilled off. The solid residue was admixed with water, adjusted with concentrated hydrochloric acid to pH 7.0 and extracted with dichloromethane. After the combined extracts had been dried with sodium sulfate, the solvent was distilled off. This resulted in 4.6 g of an oil which, according to GC, contained 0.2 g (4% of theory) of 2-chloro-4-methylphenol and 3.0 g (68% of theory) of 3-(n-butylamino)phenol. Based on the conversion of 2-chloro-4-methylphenol, the yield of 3-(n-butylamino)phenol is 71%.

Example 6

32.1 g (0.25 mol) of o-chlorophenol were slowly added dropwise under nitrogen to a mixture of 20.5 g (0.5 mol) of 95% by weight pure crystalline sodium amide and 750 ml of diethylamine. The reaction mixture was refluxed under nitrogen for 72 h with stirring. The workup comprised hydrolysis with 100 ml of saturated aqueous ammonium chloride solution, distillative removal of excess diethylamine, neutralization with dilute hydrochloric acid up to a pH of 7.5, extraction of the residue with a total of 600 ml of methylene chloride, drying over sodium sulfate and concentrating of the organic phase. Thereafter the crude oil thus obtained (46.3 g) was distilled, which yielded 31.5 g (76%) of 3-diethylaminophenol (purity>96% (GC)).

The same method can be used to obtain the compounds listed in the following table:

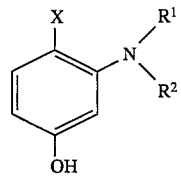

| Ex. No. | X | $NR^1R^2$ |
| --- | --- | --- |
| 7 | $CH_3$ | $NH-C_2H_5$ |
| 8 | $CH_3$ | $NH-C_3H_7$ |
| 9 | $CH_3$ | $NH-C_5H_{11}$ |

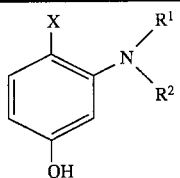

| Ex. No. | X | NR¹R² |
|---|---|---|
| 10 | $CH_3$ | $NH-C_6H_{13}$ |
| 11 | $CH_3$ | NH—cyclohexyl-H |
| 12 | $CH_3$ | $NH-C_6H_5$ |
| 13 | H | Pyrrolidino |
| 14 | H | Piperidino |
| 15 | H | N(CH₃)((CH₂)₂CH(CH₃)₂) |
| 16 | H | N(CH₃)(cyclohexyl-H) |

We claim:

1. A process for preparing carbocyclic m-aminohydroxyaromatics, which comprises reacting carbocyclic o— or m-halohydroxyaromatics or metal salts thereof with primary or secondary amines in the presence of a base and in the presence or absence of a diluent.

2. A process as claimed in claim 1, wherein the carbocyclic m-aminohydroxyaromatics conform to the formula I

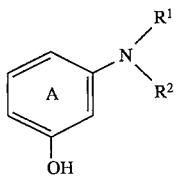

where $R^1$ and $R^2$ are each independently of the other $C_1$–$C_{18}$-alkyl, which may be substituted and may be interrupted by from 1 to 3 oxygen atoms in ether function or by from 1 to 3 $C_1$–$C_4$-alkylimino groups, $C_3$–$C_7$-cyclo-alkyl, $C_3$–$C_{18}$-alkenyl or substituted or unsubstituted phenyl, or $R^1$ and $R^2$ are together with the nitrogen atom joining them together a 5— or 6-membered saturated heterocyclic radical which may contain a further hetero atom, or else $R^1$ is hydrogen or $C_1$–$C_8$-alkanoyl, and the ring A may be substituted and may be benzofused.

3. A process as claimed in claims 1 and 2, wherein the carbocyclic o— or m-halohydroxyaromatics conform to the formula II

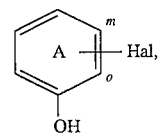

where Hal is halogen and the ring A may be substituted and may be benzofused.

4. A process as claimed in claims 1 to 3, wherein the primary or secondary amines conform to the formula III

where $R^1$ and $R^2$ are each as defined in claim 2.

5. A process as claimed in claims 1 to 4, wherein the base used is an alkali or alkaline earth metal amide, an alkali or alkaline earth metal alkoxide, an alkali or alkaline earth metal hydride, an alkali or alkaline earth organometallic compound, an alkali or alkaline earth hydroxide or an alkali or alkaline earth oxide.

6. A process as claimed in claims 1 to 5, wherein the reaction is carried out at from −50° to +300° C.

* * * * *

UNITED STATES PATENT AND TRADEMARK OFFICE
CERTIFICATE OF CORRECTION

PATENT NO. : 5,486,609
DATED : Jan. 23, 1996
INVENTOR(S) : Robert REINHARDT, et al.

It is certified that error appears in the above-indentified patent and that said Letters Patent is hereby corrected as shown below:

On the title page, Item [30], the Foreign Application Priority Data, should read:

Mar. 26, 1994 [DE] Germany.......44 10 660

Signed and Sealed this

Sixteenth Day of April, 1996

*Attest:*

BRUCE LEHMAN

*Attesting Officer*  *Commissioner of Patents and Trademarks*